United States Patent [19]  [11] Patent Number: 4,993,429
Krinsky  [45] Date of Patent: Feb. 19, 1991

[54] ORTHOTIC FITTING SYSTEM

[76] Inventor: Martin S. Krinsky, 610 Craig Ave., Campbell, Calif. 95008

[21] Appl. No.: 364,466

[22] Filed: Jun. 9, 1989

[51] Int. Cl.⁵ ............................................. A61B 5/103
[52] U.S. Cl. .................. 128/779; 12/142 N; 33/515; 73/172; 128/594
[58] Field of Search ............. 128/581, 591, 594, 779; 36/43, 44, 88, 71; 12/142 N; 73/149, 172, 290 R, 861; 33/3 B, 3 C, 512, 3 R, 515, 3 A

[56] References Cited

U.S. PATENT DOCUMENTS

| | | | |
|---|---|---|---|
| 2,558,805 | 7/1951 | Yaglou | 73/172 |
| 2,795,953 | 6/1957 | Mackowsky | 73/172 |
| 3,305,036 | 2/1967 | Walters | 73/172 |
| 4,128,951 | 12/1978 | Tansill | 36/88 X |
| 4,211,236 | 7/1980 | Krinsky | 128/594 |
| 4,426,884 | 1/1984 | Polchaninoff | 73/172 |
| 4,744,157 | 5/1988 | Dubner | 128/594 X |

Primary Examiner—Edgar S. Burr
Assistant Examiner—Moshe I. Cohen
Attorney, Agent, or Firm—Fliesler, Dubb, Meyer & Lovejoy

[57] ABSTRACT

The invention is concerned with an orthotic fitting device and method. An envelope and an adjacent diverticulum are connected to one another and are filled with a known amount of a viscous fluid. The diverticulum has indicia on it capable of indicating what portion of the fluid is within the diverticulum. The envelope is fitted against a portion of a patient's body which is to be cushioned and the fluid adjusts between the envelope and the diverticulum to provide proper cushioning for the foot. Flow communication is stopped between the diverticulum and the envelope and the amount of fluid in the diverticulum is determined from the indicia. An orthotic device in the shape of the envelope is then formulated containing the amount of fluid which remained in the envelope of the fitting device.

12 Claims, 1 Drawing Sheet

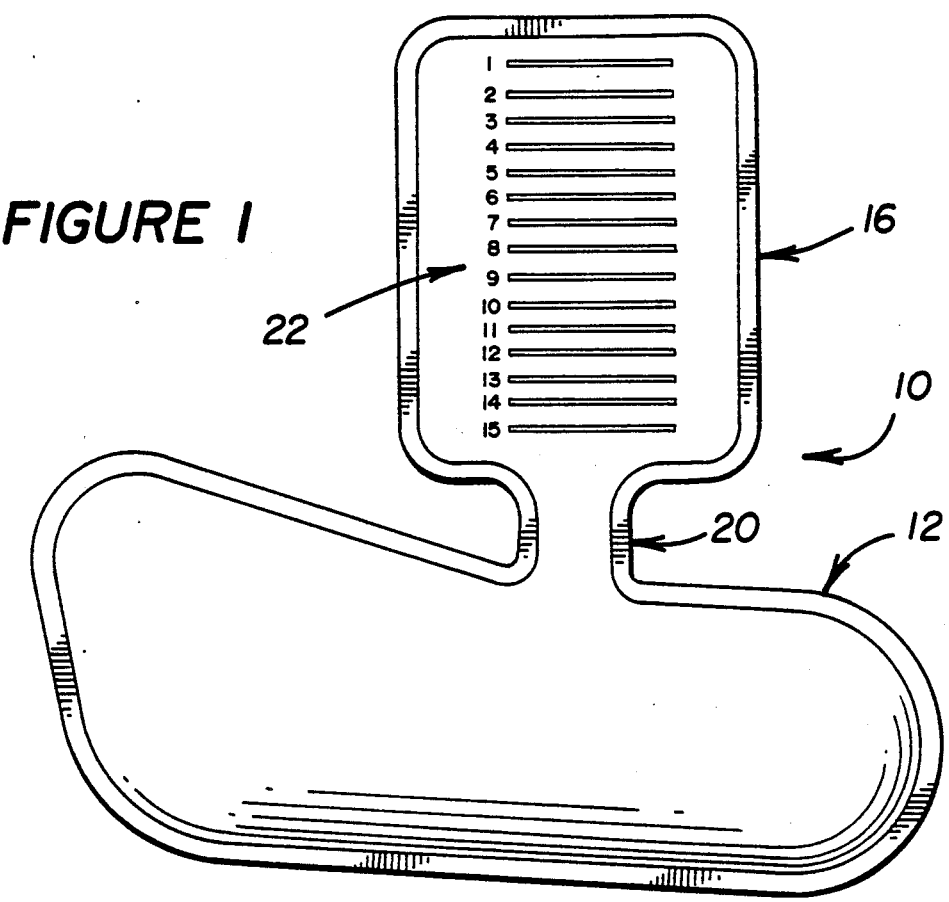
FIGURE 1
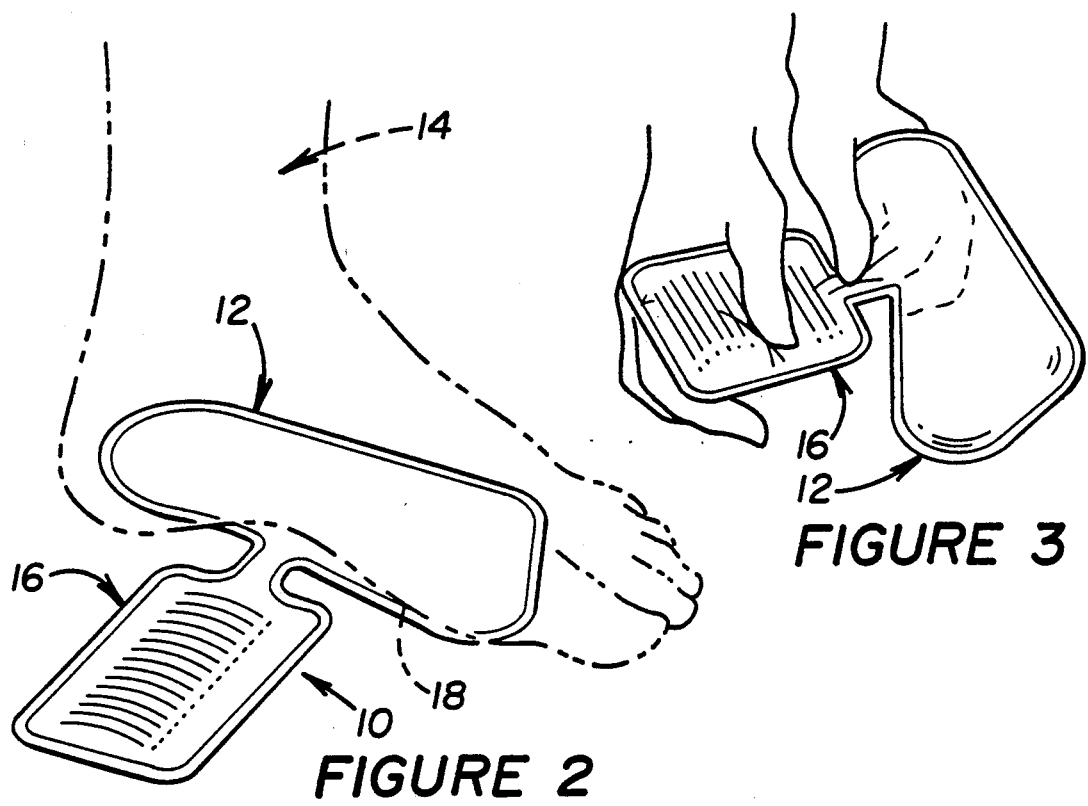
FIGURE 2
FIGURE 3

ORTHOTIC FITTING SYSTEM

TECHNICAL FIELD

The invention relates to orthopedic cushions, generally known as orthotics, and particularly to an orthotic fitting device and an orthotic fitting method for fitting an orthotic against a user's body.

BACKGROUND OF THE INVENTION

The occurrence and variety of orthopedic problems, particularly podiatric problems for human beings, are legion. Among the orthopedic problems are those incurred by amputees or by athletes. In general, many orthopedic problems may be met by assisting in the padding provided by the body's natural fatty pad and by reestablishing stability of the particular body portion.

For example, a padding assistance function of podiatric cushions aids in reducing the concentrations of weight on pressure points produced by bones in the foot, and is particularly desirable for patients with conditions such as diabetes, peripheral neuropath and fat atrophy.

Also, a podiatric cushion's function of reestablishing foot stability is particularly desirable for those persons who have a tendency to cock the foot sideways to the ground, due to a bone spur or congenital deformity such as metatarsus varus.

Various types of pads, orthotic footwear inlays and the like, are known in the art which are intended to more comfortably accommodate a portion of a user's body, such as the foot of persons encountering foot problems. U.S. Pat. No. 4,211,236, issued July 8, 1980, is concerned with a particularly useful orthopedic cushion which is comprised of a flexible envelope and an elongated member which extends outwardly from the cushion. A diverticulum opens off of the elongated member. The interiors of the envelope, elongated member and diverticulum are under partial vacuum. Within the envelope is a flowable highly viscous material. The orthopedic cushions of the aforementioned patent are fitted to a user by placing the flexible envelope containing the vacuum packed highly viscous material against the patient's body, adjusting the amount of the viscous material within the envelope between the envelope and the diverticulum as the patient's body bears against the envelope, sealing off the elongated member between the envelope and the diverticulum with a clamp, and then sending off the resulting clamped structure to the manufacturer whereat the elongated member is sealed off at the envelope, cut off and discarded. The resulting product provides sturdy, comfortable accommodation to and support of the foot. However, there is a good deal of delay in transporting the clamped structure to the sealing facility and there is the chance that the clamp will slip thus causing additional delays or leakage of the viscous material between the envelope and the diverticulum whereby the final product will not properly accommodate the user's body. Also, the manufacturer cannot simply store a number of such envelopes pre made up in different sizes and with differing amounts of enclosed fluid to fill the needs of different patients, all ready to ship or deliver in response to a prescription.

The present invention is directed to overcoming one or more of the problems as set forth above.

DISCLOSURE OF INVENTION

In accordance with an embodiment of the present invention an improvement is set forth in an orthotic fitting device having an envelope to fit against a portion of the body of a person being fitted for an orthotic device, the envelope defining an interior chamber, a diverticulum adjacent the envelope, the diverticulum having an interior chamber in flow communication with the interior chamber of the envelope, the envelope and the diverticulum being formulated of a flexible and deformable material. The improvement comprises including a known volume of a fluid within a total volume defined by the interior chambers of the envelope and diverticulum at a pressure below ambient atmospheric pressure, the volume of fluid substantially filling the total volume. The improvement further comprises providing indicia on the diverticulum, the indicia being adapted to indicate the portion of the total volume which is in the interior chamber of the diverticulum.

In accordance with another embodiment of the present invention a method is set forth of fitting an orthotic device against a portion of the body of a person. An orthotic fitting device as described above is positioned with the envelope against the portion of the body of the person being fitted with the orthotic. Flow communication is manually cut off between the envelope and the diverticulum. The indicia on the diverticulum, along with knowledge of the total volume, are utilized to determine the portion of total volume remaining in the interior chamber of the envelope A similarly sized and shaped orthotic with the quantity of the total volume which was in the interior chamber of the envelope is fitted against the portion of the body of the person being fitted for the orthotic. The similarly sized and shaped orthotic envelope is then sealed.

The orthotic fitting device and method of the present invention provide a number of advantages over the prior art. For example, each podiatrist who might wish to provide a properly designed orthotic for his patients can keep a few of the orthotic fitting devices of the present invention in his office. A few devices are necessary because of the differences in the size of feet of different persons. When a patient is to be fitted with an orthotic device the podiatrist selects the orthotic fitting device of the proper size, places the fitting device in the patients shoe, has the patient stand upon the envelope portion of the orthotic fitting device, determines the amount of the viscous fluid that is in the diverticulum and then simply calls the orthotic device manufacturer and requests an orthotic device of the proper size and with the proper amount of viscous material within the envelope. This allows the patient to receive the finished orthotic device in a minimal amount of time. Also, any problems which might occur in shipping the prior art clamped orthotic devices to the manufacturer for sealing are eliminated. Still further, the manufacturer need not operate with envelopes which are attached to elongated members which open upon diverticula in order to formulate the desired orthotic device for the patient. Instead, the manufacturer can simply take the envelope alone, fill it with the desired amount of this material and seal it off. Or, the manufacturer can simply maintain a supply of envelopes of various sizes filled with known quantities of fluid. Thus, manufacturing costs can be reduced.

BRIEF DESCRIPTION OF DRAWINGS

The invention will be better understood by reference to the figures of the drawings wherein like numbers denote like parts throughout and wherein:

FIG. 1 illustrates an orthotic fitting device in accordance with the present invention in plan view;

FIG. 2 illustrates a step in fitting an orthotic against a portion of the body of a person utilizing the orthotic fitting device of FIG. 1; and FIG. 3 illustrates another step in the orthotic device fitting method of the present invention, again utilizing the orthotic fitting device of FIG. 1.

BEST MODE FOR CARRYING OUT INVENTION

The orthotic filling device of the present invention is herein described, for convenience, as a podiatric fitting device useful for fitting an orthotic cushion to a user's foot. However, it should be understood that the orthotic fitting device is not limited to such podiatric use.

FIG. 1 illustrates an orthotic fitting device 10 having an envelope 12 adapted to fit against a portion of the body of a person 14 (FIG. 2) being fitted for an orthotic device. The envelope 12 defines an interior chamber which is in flow communication with the interior chamber of a diverticulum 16 located adjacent the envelope 12. The envelope 12 and the diverticulum 16 are formulated of a flexible and deformable material. The envelope 12 conforms generally to the outline of the foot 18 of the podiatric patient 14. It should be noted that the volume of the interior chamber of the envelope 12 and of the diverticulum 16 may vary due to the flexibility and deformability of both members. The envelope 12 and diverticulum 16 would generally be formed of a flexible deformable material such as a plastic material although elastomeric materials are also usable. For example, plastics such as a urethane film or sheeting of either ether or ester composition or polyester film or sheeting may be utilized. Urethane is particularly suitable as it is hypoallergenic and durable. The flexible and deformable material should be of sufficient thickness to provide durable and rugged use properties for the fitting device 10. For example, a thickness of from about 10 to about 35 mil when using polyurethane film has been found to be suitable.

The orthotic fitting device 10 may be formed through processes of heat sealing or laminating two layers of film or sheeting together wherein the interior chamber is formed therebetween. The general foot-like outline of envelope 12 may be formed by conventional methods such as by configuring an envelope sealing die (not illustrated) in the appropriate size and shape. Generally a set of orthotic fitting devices 10 of different sizes will be utilized by the podiatrist because of the variable sizes of patient's feet.

In the embodiment of FIG. 1 an elongated member 20 extends peripherally outwardly from one side of the envelope 12 and communicates with the diverticulum 16. In podiatric use the member 20 would normally extend from adjacent the foot's instep for ease of adjustment and use of the orthotic fitting device 10. With this construction, the orthotic fitting device 10 can be placed in a shoe and the foot 18 of the patient 14 can be placed thereover while the member 20 proceeds upwardly along the side of the foot 18 and out of the shoe adjacent the inner portion of the ankle joint. This allows fitting of the orthotic device within the particular patient's own shoe.

An alternative and generally preferred fitting method which can be carried out by a fitter is as follows:

1. Make a complete limb length measurement.
2. If a structural shortage of ¼" or more is found then this must be accommodated. This can be accomplished by placing a lift under the foot 18 of the shorter limb equal in thickness to the structural shortness.
3. Have the patient march in place to get a stance position.
4. Place the orthotic fitting device 10 parallel to the lateral border of the foot 18 with the diverticulum 16 facing the medial aspect of the foot 18. Have the patient raise the heel and slide the envelope 12 under the foot 18 so it fits under the metatarsal heads but not past the Sulcus. Place an index finger at the neck connecting the envelope 12 to the diverticulum 16; add pressure to the neck and allow the foot 18 to come down on top of the envelope 12. The posterior margin of the envelope 12 should be barely visible.
5. Have the patient supinate the foot 18 to the extreme, feeling for the Anterior Tibial tendon or the concavity of the head of the Talus and then allow pronation until the bowing of the Anterior Tibial tendon is no longer present and the head of the Talus is flush with the medial side of the foot 18.
6. Have the patient maintain this position. Release the index finger and allow the highly viscous material to be expressed from the envelope 12 to the calibrated diverticulum 16.
7. When the material flow rate begins to slow, reapply pressure with the index finger to the neck and have the patient shift body weight directly over the envelope 12. This position mimics the patients midstance position in gait. The opposite foot should not be lifted off of the ground.
8. Determine from the patient whether the support given by the envelope 12 is comfortable. If not, release small amounts of the viscous material from the envelope 12 to the diverticulum 16 until comfort is achieved.
9. Remove the envelope 12 from under the patients foot while pinching off the connecting neck and place it on a flat surface. Using the third and fourth fingers of both hands, push the expressed material to the end of the diverticulum 16 distal from the envelope 12 and read the amount of material in the diverticulum 16.

The above procedure can then be repeated for the other foot.

The orthotic fitting device 10 is filled with a known volume of a flowable, highly viscous material. The known volume of the fluid substantially fills a total volume defined by the interior chambers of the envelope 12 and the diverticulum 16 and is at a pressure below ambient atmospheric pressure. The viscous material is suitably of sufficient viscosity to reestablish stability of the wearer's foot, to disperse weight upon any one problem area, and to reduce shear forces placed upon the foot 18. The shear forces are created, for example, during a normal stride, where the foot displays a forward rocking action, the first pressure being upon the heel, and subsequent pressures moving forwardly as the foot comes down. Patients with diseases such as diabetes, peripheral neuropathy, and fat atrophy frequently require additional support beneath the foot as well as a placement of the foot in a balanced or subtalar joint neutral position. It is generally desirable to have the viscous material within the orthotic fitting device 10 as closely as possible match that which will ultimately be used in the final orthotic device since in that manner it can be assured that the amount of fluid remaining in the envelope 12 will provide the proper cushioning when the same amount of fluid is included in the final orthotic device to be used by the patient.

It has been found that the viscosity of the viscous material most suitable is from about 5000 to about 10,500 centistokes. A more viscous material, up to about 100,000 centistokes, can be used in the treatment of conditions requiring extra padding. In such instances it may be desirable to use the more viscous material in the fitting device 10. It is essential that the viscous material remains flowable and does not set within the envelope 12. Suitable materials for example are various silicone rubber polymers available from suppliers such as General Electric or Dow Corning. Silicone rubbers are particularly useful in that they are stable substances which provide a long useful life for the orthotic fitting device 10, and they are also inert so that skin damage does not occur to the patient should the silicone rubber escape from the envelope 12 during use of the orthotic fitting device 10.

Additionally, it is desirable that substantially no air bubbles be present in the viscous material within the orthotic fitting device 10 as such bubbles could interfere with the accuracy of measurement of the desirable volume for including in the orthotic device which is being used by the patient. Accordingly, the diverticulum 16, the elongated member 20 and the envelope 12 are all at a pressure below ambient atmospheric pressure so that air bubbles do not form within the orthotic fitting device 10.

In accordance with the present invention indicia 22 are provided on the diverticulum, the indicia being adapted to indicate the portion of the total volume which is in the interior chamber of the diverticulum 16.

Referring to FIG. 2 it will be noted that orthotic fitting 10 is illustrated with the foot 18 of the patient 14 Placed upon the envelope 12 and with the diverticulum 16 extending away from the foot 18. When the patient 14 stands in this manner the viscous fluid within the interior volume of the orthotic fitting device 10 equilibrates between the envelope 12 and the diverticulum 16. The amount of fluid remaining in the envelope 12 is that which is needed to provide proper cushioning under the foot 18 of the patient 14. The podiatrist then pinches off and stops flow between the envelope 12 and the diverticulum 16 as shown in FIG. 3 simply using his left thumb and index finger The podiatrist then utilizes his right thumb and index finger to squeeze the viscous fluid contained within the diverticulum 16 towards the end of the diverticulum 16 removed from the envelope 12. Next the podiatrist simple reads the indicia indicating how much viscous fluid is within the diverticulum 16. Since there is a known total volume of viscous fluid within the entire orthotic fitting device 10, the podiatrist immediately knows the precise amount of viscous fluid within the envelope 12. The podiatrist can now call the manufacturer of orthotic devices and request that the manufacturer provide an orthotic device of the proper size and having the proper quantity of viscous fluid in it for use by the particular patient. In essence a similar sized and shaped orthotic envelope is filled with the portion of the total volume which was in the interior volume of the envelope 12 of the orthotic fitting device 10 and the similarly sized and shaped orthotic envelope is sealed off.

To aid the podiatrist in being sure that he has properly pinched off communication between the envelope 12 and the diverticulum 16 it is desirable that the orthotic fitting device 10 be made of a transparent plastic material, although such is certainly not necessary.

Industrial Applicability

The present invention provides an orthotic fitting device 10 and an orthotic device fitting method suitable for fitting orthotic devices against a patient's foot 18. The device is also useful for fitting orthotic cushions against other portions of a patient's body.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. In an orthotic fitting device, having an envelope adapted to fit against a portion of the body of a person being fitted for an orthotic device, the envelope being of substantially the same size and shape as the orthotic device, the envelope defining an interior chamber, a diverticulum adjacent said envelope, the diverticulum having an interior chamber in flow communication with the interior chamber of the envelope, the envelope and the diverticulum being formulated of a flexible and deformable material, an improvement which comprises:
   including a known volume of a fluid within a total volume defined by the interior chambers of the envelope and the diverticulum at a pressure below ambient atmospheric pressure, said volume of fluid substantially filling said total volume; and
   providing indicia on said diverticulum, said indicia being adapted to indicate the portion of said total volume which is in said interior chamber of said diverticulum.

2. An orthotic fitting device as set forth in claim 1, wherein said material is transparent.

3. An orthotic fitting device as set forth in claim 1, wherein said fluid has a viscosity which falls within a range from about 5000 centistokes to about 10,500 centistokes.

4. A method of fitting an orthotic against a portion of the body of a person, comprising:
   positioning an orthotic fitting device having an envelope adapted to fit against the portion of the body of the person being fitted for an orthotic device, the envelope defining an interior chamber, a diverticulum adjacent said envelope, said diverticulum having an interior chamber in flow communication with the interior chamber of the envelope, the envelope and the diverticulum being formulated of a flexible and deformable material, a known volume of fluid filling a total volume defined by the interior chambers of the envelope and the diverticulum at a pressure below ambient atmospheric pressure, the diverticulum having indicia thereon which are adapted to indicate the amount of said total volume which is in said interior chamber of said diverticulum, with the envelope against the portion of the body of the person being fitted with the orthotic;

manually cutting off flow communication between said envelope and said diverticulum;

utilizing said indicia and knowledge of the total volume to determine the quantity of said total volume remaining in said interior chamber of said envelope;

fitting an orthotic which is similarly sized and shaped as said envelope with the quantity of said total volume which was in said interior chamber of said envelope against the portion of the body of the person being fitted with the orthotic.

5. A method as set forth in claim 4, wherein said envelope and said diverticulum are transparent.

6. A method as set forth in claim 4, wherein said fluid has a viscosity which falls within a range from about 5000 centistokes to about 10,500 centistokes.

7. A method as set forth in claim 4, further including preparing said orthotic by:

filling a similarly sized and shaped orthotic envelope with the quantity of said total volume which was in said interior chamber; and sealing said similarly sized and shaped orthotic envelope to produce said orthotic.

8. An apparatus for fitting an orthotic device to a patient's body part, said apparatus comprising:

an envelope formed of opposing sheets of flexible material, including an interior chamber within said sheets, said envelope being adapted to fit against said body part, said envelope having dimensions substantially equal to dimensions of said orthotic device;

a diverticulum having an interior chamber in flow communication with said interior chamber of said envelope said diverticulum and said envelope are formed from said opposing sheets as a unitary construction;

a predetermined total quantity of fluid within said envelope and diverticulum, which fluid may flow between said interior chambers thereof;

indicia means, affixed to said diverticulum, for measuring a quantity of said fluid which is within one of said envelope and said diverticulum.

9. The apparatus of claim 8 wherein:

said indicia means measures a quantity of said fluid within said diverticulum, to indicate a remaining quantity of said fluid which is within said envelope by the relationship of:

FE=FT−FD;

wherein FT is the predetermined total quantity of said fluid, FD is the quantity of fluid in said diverticulum as measured by said indicia means, and FE is the remaining quantity of fluid in said envelope.

10. A method of measuring a patient's body part for fitting an orthotic device thereto using an apparatus which includes an envelope formed of opposing sheets of flexible material, including (A) an interior chamber within said sheets, said envelope having dimensions substantially equal to dimensions of said orthotic device, (B) a diverticulum having an interior chamber in flow communication with said interior chamber of said envelope, (C) a predetermined total quantity of fluid within said envelope and diverticulum, which fluid may flow between said interior chambers thereof, and (D) indicia means, affixed to said diverticulum, for measuring a quantity of said fluid which is within one of said envelope and said diverticulum, said indicia means measures a quantity of said fluid within said diverticulum, to indicate a remaining quantity of said fluid which is within said envelope by the relationship of FE=FT−FD wherein FT is the predetermined total quantity of said fluid, FD is the quantity of fluid in said diverticulum as measured by said indicia means, and FE is the remaining quantity of fluid in said envelope, said method comprising the steps of:

enclosing within said envelope an excess amount of said fluid relative to an amount needed to properly fit said envelope to said body part;

positioning said envelope into contact with said body part, with force sufficient to form at least one of said flexible sheets to contours of said body part, said fluid flowing within said envelope generally away from said at least one sheet in response to localized pressure thereon;

pressing said at least one sheet against said body part until said fluid flows from said envelope into said diverticulum in an amount sufficient to properly fit said envelope to said body part;

measuring said amount of fluid FD;

determining, according to said measuring step, how much fluid FE remains in said envelope;

placing into said orthotic device an amount of fluid substantially equal to said determined amount of fluid FE, to achieve a fit of said orthotic device to said body part substantially equivalent to the proper fit achieved by said pressing step.

11. The method of claim 10, wherein said indicia means include parallel hash marks across said diverticulum, and said measuring step comprises:

temporarily interrupting fluid flow from said envelope to said diverticulum;

squeezing said fluid FD in said diverticulum into a farthest possible position from said envelope; and observing a given hash mark which most nearly parallels an edge of said fluid FD nearest said envelope.

12. The method of claim 10, wherein said envelope and said orthotic device have proper dimensions for use as an in-shoe podiatric cushion, and wherein:

said positioning step includes inserting said envelope into a shoe such as the patient may typically wear, and inserting the patient's foot into said shoe and onto said envelope; and said pressing step includes the patient standing on said foot and onto said envelope.

* * * * *